United States Patent [19]

Backhouse et al.

[11] Patent Number: 5,287,967
[45] Date of Patent: Feb. 22, 1994

[54] BAG CONTAINING THREE COMPONENT BIOCIDAL COMPOSITION

[75] Inventors: Bryan S. Backhouse, Leefdaal, Belgium; William A. Fern, Bamford, England

[73] Assignee: Imperial Chemical Industries PLC, London, England

[21] Appl. No.: 970,449

[22] Filed: Nov. 2, 1992

Related U.S. Application Data

[62] Division of Ser. No. 536,132, Jun. 11, 1990, Pat. No. 5,185,356.

[30] Foreign Application Priority Data

Jun. 13, 1989 [GB] United Kingdom ............... 8913513

[51] Int. Cl.$^5$ .................. B65D 85/84; A61K 31/425
[52] U.S. Cl. .................. 206/524.7; 514/301; 514/372; 514/373
[58] Field of Search ........... 514/301, 372, 373; 546/114; 548/209, 213; 206/828, 524.7

[56] References Cited

U.S. PATENT DOCUMENTS 4,310,590 1/1982 Petigara ................. 546/209

Primary Examiner—Nicholas S. Rizzo
Assistant Examiner—Y. N. Gupta
Attorney, Agent, or Firm—Cushman, Darby & Cushman

[57] ABSTRACT

A particulate composition comprising an isothiazolinone or isothiazolothione or a salt or complex thereof and a water soluble metal salt. The salt is typically a metal salt, for example the sodium salt of 1,2-benzisothiazolin-3-one and the water soluble metal salt is particularly an alkali metal salt such as disodium hydrogen phosphate. A preferred composition can be obtained by stirring together an isothiazolinone or isothiazolothione, a base and an alkali metal phosphate in the presence of water until a dry particulate product is obtained. The particulate product is typically highly and rapidly soluble in water and may be stored in a container formed from a water soluble material, for example a bag formed from polyvinyl alcohol.

12 Claims, No Drawings

BAG CONTAINING THREE COMPONENT BIOCIDAL COMPOSITION

This is a divisional of co-pending application Ser. No. 07/536,132 filed on Jun. 11, 1990, now U.S. Pat. No. 5,185,356.

The present invention relates to compositions and in particular to solid particulate compositions which are useful as industrial biocides.

Industrial biocides are useful to prevent industrial spoilage in particular that caused by bacteria and fungi. Industrial biocides find application, inter alia, in the preservation of paints, latices, adhesives, leather, wood, metal working fluids, cooling water and plastics materials.

One class of compound which can be useful as an industrial biocide is based on the isothiazolinone structure for example 5-chloro-2-methylisothiazolin-3-one; 4,5-dichloro-2-methylisothiazolin-3-one; 1,2-benzisothiazolin-3-one and 4,5-trimethylene-4-isothiazolin-3-one. In many applications an industrial biocide is used in a liquid medium, particularly in an aqueous medium and for such applications it is desirable to be able to meter the biocide into the medium to be protected by the biocide. Metering is conveniently effected using a solution of the biocide, especially an aqueous solution. However, the water solubility of some isothiazolinone compounds is limited and although certain salts thereof, particularly amine salts and alkali metal salts, have a higher solubility, this is still somewhat limited, especially at temperatures of 0° C. and below. There have been a number of proposals to use systems containing alkanolamines (GB 1191253), diamines (GB 1330531) and glycols (GB 2004747), and these have resulted in solutions of improved physical stability. However such systems require the use of considerable quantities of organic solvent and this is undesirable commercially.

Isothiazolinones may be obtained in an unpurified form as an aqueous dispersion or paste and this is satisfactory for some applications. However, these dispersions or pastes tend to settle out on standing, thus making accurate metering difficult. Furthermore, the dispersions and pastes may have variable physical properties which can give rise to handling or other problems in use.

The provision of an isothiazolinone as a particulate solid is a possible method of overcoming difficulties of obtaining stable, cost-effective solutions or satisfactory dispersions or pastes. Hitherto it has been difficult to provide such a particulate solid due to the requirements of industrial hygiene which necessitate containment of the dried solid. Furthermore, some isothiazolinone compounds having inadequate stability when in the dry state.

It is the object of the present invention to provide a particulate solid containing an isothiazolinone.

According to the present invention there is provided a particulate solid comprising (a) an isothiazolinone or an isothiazolothione derivative, or a salt or complex thereof, and (b) a water soluble inorganic salt which does not form a water insoluble salt or water insoluble complex with the isothiazolinone, isothiazolothione or salt or complex.

The isothiazolinone or isothiazolothione derivative which is component (a) of the particulate solid is typically a compound of the general formula:

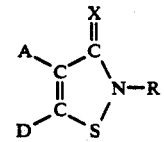

or a salt or complex thereof; wherein:

X is an oxygen or sulphur atom;

R is a hydrogen atom, a substituted or unsubstituted hydrocarbyl group, a substituted or unsubstituted hydrocarbylthio group, a substituted or unsubstituted hydrocarbyloxy group, or a carbamoyl group;

A is a hydrogen atom, a halogen atom, a cyano group, or a substituted or unsubstituted hydrocarbyl group;

D is a hydrogen atom, a halogen atom, a cyano group, or a substituted or unsubstituted hydrocarbyl group; or A and D, together with the carbon atoms to which they are attached, form a five- or six-membered ring, which may optionally be substituted.

Preferably component (a) is at least one isothiazolinone derivative, that is a compound in which X is an oxygen atom. If the groups R, A and D are, or contain, substituted hydrocarbyl groups, the substituents are typically halogen, alkoxy or alkylthio, particularly those in which the alkyl groups contain 1 to 4 carbon atoms. If R is a carbamoyl group, this is of the general type $-CONHR^1$ where $R^1$ is a hydrogen atom or a hydrocarbyl group, which may be substituted. It is generally preferred that the group R is a hydrogen atom or a lower alkyl group, that is an alkyl group containing 1 to 4 carbon atoms. R is especially hydrogen or a methyl group.

A and D may, together with the carbon atoms to which they are attached, form a five- or six-membered ring, which may be substituted, the substituents typically being halogen, alkyl, alkoxy or alkylthio groups. The ring thus obtained may contain a heteroatom for example a nitrogen atom but in general A and D form a hydrocarbon ring such as a benzene, cyclopentene or cyclohexene ring. Alternatively, A and D are separate groups and one or both of A and D can be a hydrogen atom. It is generally preferred that at least one of A and D is other than a hydrogen atom and is, particularly, a halogen atom, for example chlorine, or a lower alkyl group.

Compounds which can be used as a component (a) of the particulate solid include 5-chloro-2-methylisothiazolin-3-one (R is methyl, A is hydrogen and D is chlorine); 4,5-dichloro-2-methylisothiazolin-3-one (R is methyl and A and D are both chlorine); 2-n-octylisothiazolin-3-one (R is n-octyl, A and D are both hydrogen); 1,2-benzisothiazolin-3-one (R is hydrogen and A and D, together with the carbon atoms to which they are attached, form a benzene ring); 4,5-trimethylene-4-isothiazolin-3-one (R is hydrogen and A and D, together with the carbon atoms to which they are attached, form a cyclopentene ring); and 2-methyl-4,5-trimethylene-4-isothiazolin-3-one (R is methyl and A and D, together with the carbon atoms to which they are attached, form a cyclopentene ring).

The component (a) is especially one in which R is hydrogen and A and D together form an unsubstituted five- or six membered, hydrocarbon ring, for example as in 1,2-benzisothiazolin-3-one and 4,5-trimethylene-4-isothiazolin-3-one.

Some isothiazolinone or isothiazolothione compounds which may be used as component (a) have improved solubility in water when in the form of a salt or complex. The salt or complex may be with any suitable cation for example an amine (including an alkanolamine) or a metal. It is preferred that a metal salt or complex is with a monovalent metal, especially an alkali metal. The alkali metal salt may be a lithium, sodium or potassium salt but it is generally preferred to use a sodium salt in view of the ready availability of suitable sodium compounds from which to prepare the salt.

Some isothiazolinone or isothiazolothione compounds which can be used as component (a) are susceptible to alkaline conditions and decompose in the presence of alkali.

The water-soluble inorganic salt which is component (b) of the particulate solid of the present invention should not form a water insoluble salt or water insoluble complex with component (a). Furthermore, the salt should be compatible with component (a) and should be such as to buffer the pH of an aqueous solution at a value at which component (a) is soluble and is stable.

Salts of divalent metals may form water insoluble salts with certain isothiazolinones or isothiazolothiones which can be used as component (a). Hence, such salts are not always suitable for use as component (b). However, we have found that some salts of divalent metals can be used as component (b) without forming a water insoluble salt with component (a). Thus, we have obtained a soluble system when using magnesium sulphate as component (b). Preferred salts are alkali metal salts. The salts should not give a pH which results in the isothiazolinone or isothiazolothione being in an insoluble form or decomposing. Thus, for compounds which are unstable in an alkaline medium, the salt should be a neutral or acid salt, for example sodium sulphate or, more preferred, sodium dihydrogen phosphate. In contrast, some isothiazolinone compounds are insoluble in acid media and hence the salt should be neutral or preferably, basic, for example disodium hydrogen phosphate.

Particulate solids in accordance with the present invention include those in which component (a) is 5-chloro-2-methylisothiazolin-3-one, or 4,5-dichloro-2-methylisothiazolin-3-one and component (b) is an acidic salt.

Other particulate solids include those in which component (a) is a salt or complex, preferably an alkali metal salt, of 1,2-benzisothiazolin-3-one or 4,5-trimethylene-4-isothiazolin-3-one and component (b) is an alkali salt.

A preferred particulate solid in accordance with the present invention is one in which component (a) is the sodium salt of 1,2-benzisothiazolin-3-one and component (b) is disodium hydrogen phosphate.

The particulate solid may include other components in addition to the isothiazolinone or isothiazolothione derivative and water-soluble inorganic salt. The particulate solid may contain an appreciable proportion of absorbed water, for example from 10 to 45% by weight of water. However, the proportion of water present in the solid should not be such as to adversely affect the flow properties of the solid. The water content of the particulate solid can be in the range 20 to 40% by weight of the particulate solid.

The proportion of component (a) which is present in the particulate solid may be up to about 45% by weight of the particulate solid. The proportion of component (a) is typically at least 10% by weight of the particulate solid and it is preferred that component (a) is present in an amount of at least 20% by weight of the particulate solid. Especially preferred particulate solids in accordance with the present invention contain 25 to 40% by weight of component (a).

Component (b) of the particulate solid is typically present in an amount of at least 10% by weight. In general the proportion of component (b) does not exceed 50% by weight of the particulate solid. We have obtained particulate solids having useful properties which contained 20 to 35% by weight of component (b).

In addition to containing components (a) and (b), and typically also water, the particulate solid may contain other components in a minor proportion of not more than 2% by weight of each of the other components. One such other component which may be present is a de-dusting agent. Suitable de-dusting agents include dodecyl benzene, tridecyl octadecanoate, trimethylol propane tridodecanoate, condensates of beta-naphthol with ethylene oxide, twichel oil, Ensitol USN and mineral oil. The de-dusting agent is particularly useful if the particulate solid contains fine particles since these are agglomerated by de-dusting agents and the level of dust is reduced.

Preferred amounts of the de-dusting agent are 0.5 to 1.5% by weight, for example about 1% by weight relative to the weight of the particulate solid including the de-dusting agent.

A preferred particulate solid in accordance with the present invention contains the sodium salt of 1,2-benzisothiazolin-3-one, disodium hydrogen phosphate, water and a de-dusting agent.

In the preferred particulate solid, the sodium salt of 1,2-benzisothiazolin-3-one is present in an amount of 25 to 40% by weight; disodium hydrogen phosphate is present in an amount of 20 to 35% by weight; water is present in an amount of 20 to 40% by weight and a de-dusting agent in an amount of 0.5 to 1.5% by weight. In general the foregoing components aggregate to 100% by weight of the particulate solid.

As discussed in more detail hereafter, the particulate solid is obtained by blending together the components thereof, or precursors of the components, under appropriate conditions. One of the components is the water-soluble inorganic salt which is blended as a particulate solid and we have found that the particle size of the final product depends on the original particle size of the water-soluble inorganic salt.

The particulate solid of the present invention is preferably a free-flowing solid which, particularly in the absence of a de-dusting agent, shows little tendency to agglomeration. The particle size of the particulate solid is preferably such that no particle exceeds 1 mm in size. An especially preferred solid is one having a mean particle size in the range 100 to 500 micrometers and most preferably in the range 250 to 400 micrometers. The particle size of the starting water-soluble inorganic salt component should be selected to give the desired final particle size.

It is a particularly desirable feature of the particulate solid of the present invention that it is readily soluble in water. Thus, the solid is preferably such that it will dissolve essentially completely in water at ambient temperature, that is 15° to 25° C., to give an isothiazolinone or isothiazolothione concentration of 1000 ppm w/v in a time of not more than 5 minutes, and preferably in not more than 2 minutes. However, it will be appreciated that the amount of particulate solid added should be such as to give a desired concentration of the isothiazolinone or isothiazolothione and this may be greater or, typically, less than 1000 ppm w/v and for many systems is preferably not more than 350 ppm w/v. When the isothiazolinone is 1,2-benzisothiazolin-3-one, the concentration thereof is preferably in the range from 30 ppm up to 300 ppm w/v. With other compounds, the preferred concentration may be higher or lower depending on the particular compound.

The particulate solid may absorb atmospheric water vapour and if this is not prevented the particulate solid may become a sticky paste. To minimise this possibility and also to minimise environmental problems due to the characteristics of the isothiazolinone or isothiazolothione, the particulate solid is preferably packaged in suitable containers. To reduce environmental handling problems still further, the particulate solid can be packaged in desired quantities in suitable bags which, to reduce handling of the particulate solid to a single stage, are very conveniently formed of a water soluble material. The particulate solid can be packaged in any suitable amount depending on the proposed application and scale of use. Thus, the particulate solid may be packaged in amounts from 5 g up to 5 kg and in general will be packaged in an amount of from 50 g up to 500 g.

The particulate solid is typically used to provide anti-microbial properties to an aqueous medium. A solution containing a desired level of the biocidally active component, that is the isothiazolinone or isothiazolothione, is conveniently obtained by adding a predetermined number of bags containing a known amount of the particulate solid to a known volume of water and stirring the mixture. Using bags formed of a water-soluble material, the bag dissolves permitting the particulate solid to dissolve with no further handling of the particulate solid.

Thus, as a further aspect of the present invention, the particulate solid is packaged and sealed in bags formed from a water-soluble material.

The water-soluble material from which the bags are formed may be any suitable product of this type including, for example, polyethylene oxide, methyl cellulose, polyvinyl alcohol or polyvinyl acetate.

Each bag contains a discrete, known dosage of the particulate solid. The bags are preferably further packaged, for example, in a drum lined with a plastic material such as polyvinyl chloride.

The particulate solid may be prepared by blending together the components thereof or precursors. If the particulate solid contains essentially no water and both components are solid, the particulate solid may be prepared using any suitable solids blending technique, for example by tumble blending or by high speed mixing.

In general however, the isothiazolinone or isothiazolothione starting material typically contains appreciable quantities of water, and during the blending operation the mixture forms a thick viscous paste before the particulate solid is finally obtained. In order to mix materials of this type it is necessary to use a mixer which is capable of processing a wide range of physical forms which are produced at various stages during the mixing process. Accordingly, suitable mixers are of the paste mixer type and preferably are mixers having a self-cleaning agitator design of mixer blade. Suitable mixers of this type include Z-blade mixers, for example those available from Baker Perkins or Beken. Alternatively, a bulk type mixer having a circulating wall agitator can be used, such a mixer being available from Nauta.

If the isothiazolinone or isothiazolothione is to be incorporated into the particulate solid as a salt or complex, mixing is conveniently effected by first mixing together the isothiazolinone or isothiazolothione with a base, for example a metal hydroxide such as an alkali metal hydroxide, thereafter adding the water-soluble inorganic salt and continuing to mix until the mixture becomes a particulate solid. When using 1,2-benzisothiazolin-3-one, this is available in concentrated form as a paste containing at least 50% by weight, and preferably at least 60% by weight, of 1,2-benzisothiazolin-3-one the remainder being water together with residual quantities of impurities resulting from the production of the 1,2-benzisothiazolin-3-one. The base is very preferably sodium hydroxide which is conveniently used as a concentrated aqueous solution, typically containing at least 35% by weight, and especially from 40% up to 50% by weight, of sodium hydroxide. These two materials form a thick paste on being mixed. Mixing is continued for a sufficient time, for example 0.25 to 5 hours, to allow reaction of the 1,2-benzisothiazolin-3-one and the base to form the sodium salt of 1,2-benzisothiazolin-3-one. The water-soluble metal salt is added and mixed for a sufficient time to absorb the water and form a particulate solid product. The water-soluble metal salt is desirably a salt having a low degree of hydration and it is preferred that the water-soluble metal salt is an anhydrous material especially a hygroscopic material. A particularly useful water-soluble metal salt for use with the sodium salt of 1,2-benzisothiazolin-3-one is anhydrous disodium hydrogen phosphate. Mixing with the water-soluble metal salt is typically effected for 0.25 to 5 hours, for example for about one hour. The initial stage of mixing with a base is omitted if it is not desired to form a salt or complex of the isothiazolinone or isothiazolothione.

Before being discharged from the mixing vessel, a small proportion, for example up to 2% by weight, of a de-dusting agent is preferably added and mixing is continued for a short period of time which is typically not more than one hour, for example 1 to 20 minutes.

Some of the isothiazolinones and isothiazolothiones which are component (a) of the particulate solid have undesirable characteristics, for example some may cause skin sensitisation and generally handling of these materials is effected under a high level of containment. As noted previously herein, handling of the particulate solid may be reduced by packaging the solid, in desired quantities, in water-soluble bags. Hence, after preparing the particulate solid it is preferably transferred to a bag filling line and packaged in bags, preferably water-soluble bags, which are then sealed. The bags may be handled with a greater margin of safety and a decreased requirement for a high level of containment, subject to avoiding damage to the bag and spillage of the contents.

The particulate solid, or bags of particulate solid, may then be used to provide protection against microbial attack. The use of isothiazolinones to provide protection against bacteria is known and the particulate solid, or bags thereof, may be used in accordance with the known procedures, for example by dissolving the particulate solid or bags thereof in an aqueous medium the components of which require protection against bacterial-induced deterioration.

Various aspects of the present invention are set out in more detail hereafter in the following illustrative examples in which all parts and percentages are by weight unless otherwise stated.

EXAMPLE 1

Mixing was effected using a horizontal Z-Blade mixer available from Beken and having a capacity of about 0.5 $dm^3$.

102 g of a paste of 1,2-benzisothiazolin-3-one and water containing 27.44 g of water, the remainder being 1,2-benzisothiazolin-3-one, was charged to the mixer, followed by 40 g of distilled water and 50 g of aqueous sodium hydroxide containing 23.5 g of sodium hydroxide.

A thick paste was obtained and this was mixed for a time of one hour. 75 g of anhydrous disodium hydrogen phosphate was added to the contents of the mixer and mixing was continued for a further hour. 2.67 g of a condensate of beta-naphthol with 10 moles of ethylene oxide were added to the contents of the mixer, which was a dry particulate solid at this stage, and mixing was continued for a further ten minutes.

The mixture was discharged from the Beken mixer as an off white, particulate solid which, by analysis, was found to contain 30.9% of 1,2-benzisothiazolin-3-one.

2.3 g of the resulting particulate solid was added to one $dm^3$ of distilled water which was being agitated at about 80 r.p.m. using a magnetic stirrer. The solid dissolved in 70 seconds. The resulting solution had a pH of 10.3. The concentration of the sodium salt of 1,2-benzisothiazolin-3-one was found to be 710 ppm.

EXAMPLE 2

Samples of the particulate solid obtained as described in Example 1 were packed in polyvinyl alcohol bags in an amount of 10 g of solid in each bag.

One bag was added to one $dm^3$ of distilled water which was being agitated at about 80 r.p.m. using a magnetic stirrer.

The bag dissolved in 20 seconds and the powder had completely dissolved in a further 120 seconds to give a concentration of the sodium salt of 1,2-benzisothiazolin-3-one of about 3500 ppm.

EXAMPLES 3 TO 6

The procedure described in Example 1 was repeated with the exception that the anhydrous disodium hydrogen phosphate was replaced by the same amount of anhydrous sodium sulphate, anhydrous sodium carbonate, anhydrous magnesium sulphate or anhydrous trisodium phosphate.

Using anhydrous sodium sulphate and anhydrous sodium carbonate, the initial product was somewhat pasty but on allowing to stand overnight in a sealed container, a dry particulate product was obtained.

In all cases the particulate solid was readily soluble in water using the test procedure described in Example 1.

By way of comparison, using either magnesium chloride or magnesium acetate the particulate solid obtained was not readily soluble and remained essentially undissolved under the conditions described in Example 1.

EXAMPLE 7

The procedure of Example 1 was repeated with the exception that the anhydrous disodium hydrogen phosphate was replaced by 1.5 times the amount of sodium dihydrogen phosphate dihydrate. A dry particulate solid was obtained as in Example 1.

EXAMPLES 8 TO 11

A product obtained by the process of Example 1 was added to 50 g aliquots of an exterior acrylic emulsion paint (based on Revacryl 1A latex at pH9) containing 0.2% yeast extract. The product was added to the paint in amounts to give a level of 1,2-benzisothiazolin-3-one of 125, 250, 500 or 750 ppm w/v in the paint. The paint mixture containing the added product was then inoculated with a mixture of bacteria.

The inoculum was a mixed suspension of bacteria which had been prepared by mixing equal amounts of suspensions each of which contained a different one of the bacteria *Aeromonas hydrophila, Proteus rettgeri, Pseudomonas aeruginosa, Serratia marcescens, Alcaligenes spp, Pseudomonas cepacia* and *Pseudomonas putida*.

Each paint mixture was inoculated with 1 $cm^3$ of the mixed bacterial suspension and incubated at 30° C. After contact times of one, three and seven days, a small aliquot of the paint mixture was removed and examined for bacterial growth. The extent of growth of bacteria was recorded. After removal of the seven day aliquot, a further 1 $cm^3$ of the mixed bacterial suspension was added. Aliquots were removed after one, three and seven days of the second week. At the end of the second week, a further 1 $cm^3$ of the mixed bacterial suspension was added. Aliquots were removed after one, three and seven days of the third week. The results obtained are set out hereafter in Table One.

For comparative purposes, further paint mixtures were prepared using a 20% by weight solution of the sodium salt of 1,2-benzisothiazolin-3-one in aqueous dipropylene glycol.

TABLE ONE

| Ex. or Comp Ex | Disp (a) Type | (ppm) (b) | Bacterial growth (c) | | | | | | | | |
|---|---|---|---|---|---|---|---|---|---|---|---|
| | | | Week 1 Day | | | Week 2 Day | | | Week 3 Day | | |
| | | | 1 | 3 | 7 | 1 | 3 | 7 | 1 | 3 | 7 |
| 8 | 1 | 750 | 0 | 0 | 0 | 0 | 0 | 0 | 0 | 0 | 0 |
| 9 | 1 | 500 | 0 | 0 | 0 | 0 | 0 | 0 | 0 | 0 | 0 |
| 10 | 1 | 250 | 3 | 3 | 3 | 3 | 3 | 3 | 3 | 3 | 3 |
| 11 | 1 | 125 | 4 | 4 | 4 | 4 | 4 | 4 | 4 | 4 | 4 |
| A | BT | 750 | 0 | 0 | 0 | 0 | 0 | 0 | 0 | 0 | 0 |
| B | BT | 500 | 0 | 0 | 0 | 0 | 0 | 0 | 0 | 0 | 0 |
| C | BT | 250 | 0 | 0 | 0 | 2 | 2 | 0 | 1 | 1 | 0 |
| D | BT | 125 | 3 | 3 | 2 | 3 | 3 | 2 | 3 | 3 | 0 |

Notes to Table One
(a) 1 is the product of Example 1 BT is a 20% by weight solution of the sodium salt of 1,2-benzisothiazolin-3-one in aqueous dipropylene glycol.
(b) The quantities are given as ppm w/v relative to the paint mixture of the 1,2-benzisothiazolin-3-one component of the added component.
(c) 0 means no growth (no visible colonies).
1 means a trace of growth visible.
2 means a light growth (a few colonies visible).
3 means moderate growth (discrete colonies visible, possibly with some coalescence).
4 means dense/confluent growth (coalescing colonies visible throughout).

EXAMPLES 12 TO 15

The procedure described for Examples 8 to 11 was repeated with the exception that the acrylic emulsion paint containing yeast extract was replaced by a polyvinylacetate aqueous emulsion paint formulation which did not contain yeast extract.

The results obtained are set out hereafter in Table Two.

TABLE TWO

| Ex. or Comp Ex | Disp (a) Type | (ppm) (b) | Bacterial growth (c) | | | | | | | | |
|---|---|---|---|---|---|---|---|---|---|---|---|
| | | | Week 1 Day | | | Week 2 Day | | | Week 3 Day | | |
| | | | 1 | 3 | 7 | 1 | 3 | 7 | 1 | 3 | 7 |
| 12 | 1 | 750 | 0 | 0 | 0 | 2 | 0 | 0 | 0 | 0 | 0 |
| 13 | 1 | 500 | 0 | 0 | 0 | 3 | 2 | 0 | 0 | 0 | 0 |
| 14 | 1 | 250 | 2 | 2 | 0 | 4 | 4 | 4 | 4 | 4 | 4 |
| 15 | 1 | 125 | 4 | 4 | 4 | 4 | 4 | 4 | 4 | 4 | 4 |
| E | BT | 750 | 0 | 0 | 0 | 2 | 2 | 0 | 0 | 0 | 0 |
| F | 8T | 500 | 0 | 0 | 0 | 2 | 2 | 0 | 2 | 1 | 0 |
| G | 8T | 250 | 0 | 0 | 0 | 2 | 2 | 3 | 4 | 4 | 4 |
| H | BT | 125 | 2 | 2 | 3 | 4 | 4 | 4 | 4 | 4 | 4 |

Notes to Table Two
a, b and c are all as defined in Notes to Table One.

EXAMPLES 16 TO 24

The procedure described for Examples 8 to 11 was repeated with the exception that the product was added in amounts to give a level of 1,2-benzisothiazolin-3-one of 100, 150, 200, 250, 300, 350, 400, 450 and 500 ppm w/v in the paint.

The results obtained are set out hereafter in Table Three.

TABLE THREE

| Ex. or Comp Ex | Disp (a) Type | (ppm) (b) | Bacterial growth (c) | | | | | | | | |
|---|---|---|---|---|---|---|---|---|---|---|---|
| | | | Week 1 Day | | | Week 2 Day | | | Week 3 Day | | |
| | | | 1 | 3 | 7 | 1 | 3 | 7 | 1 | 3 | 7 |
| 16 | 1 | 500 | 0 | 0 | 0 | 2 | 0 | 0 | 1 | 0 | 0 |
| 17 | 1 | 450 | 0 | 0 | 0 | 2 | 0 | 0 | 2 | 0 | 0 |
| 18 | 1 | 400 | 0 | 0 | 0 | 2 | 2 | 1 | 2 | 2 | 1 |
| 19 | 1 | 350 | 0 | 0 | 0 | 3 | 2 | 1 | 3 | 3 | 2 |
| 20 | 1 | 300 | 0 | 0 | 0 | 3 | 3 | 2 | 3 | 3 | 3 |
| 21 | 1 | 250 | 0 | 0 | 0 | 3 | 3 | 3 | 3 | NM | NM |
| 22 | 1 | 200 | 0 | 0 | 0 | 3 | 4 | 3 | 4 | NM | NM |
| 23 | 1 | 150 | 0 | 0 | 0 | 3 | 4 | 4 | 4 | NM | NM |
| 24 | 1 | 100 | 2 | 3 | 4 | 4 | 4 | 4 | 4 | NM | NM |
| I | BT | 500 | 0 | 0 | 0 | 1 | 0 | 0 | 1 | 0 | 0 |
| J | BT | 450 | 0 | 0 | 0 | 1 | 0 | 0 | 1 | 0 | 0 |
| K | BT | 400 | 0 | 0 | 0 | 2 | 0 | 0 | 2 | 0 | 0 |
| L | BT | 350 | 0 | 0 | 0 | 2 | 0 | 0 | 3 | 0 | 0 |
| M | BT | 300 | 0 | 0 | 0 | 2 | 0 | 0 | 2 | 2 | 1 |
| N | BT | 250 | 0 | 0 | 0 | 3 | 2 | 1 | 3 | 2 | 2 |
| O | BT | 200 | 0 | 0 | 0 | 3 | 3 | 3 | 3 | NM | NM |
| P | BT | 150 | 0 | 0 | 0 | 4 | 4 | 4 | 4 | NM | NM |
| Q | BT | 100 | 0 | 1 | 2 | 4 | 4 | 4 | 4 | NM | NM |
| R | NIL | NIL | 4 | 4 | 4 | 4 | 4 | 4 | 4 | 4 | 4 |

Notes to Table Three
a, b and c are all as defined in Notes to Table One
NM means no measurement made.

EXAMPLES 25 TO 30

The procedure described for Examples 16 to 24 was repeated with the exception that the acrylic emulsion paint containing yeast extract was replaced by a polyvinylacetate aqueous emulsion paint formulation which did not contain yeast extract and the minimum level of additive used corresponded to 200 ppm w/v of 1,2-benzisothiazolin-3-one in the paint.

The results obtained are set out hereafter in Table Four.

TABLE FOUR

| Ex. or Comp Ex | Disp (a) Type | (ppm) (b) | Bacterial growth (c) | | | | | | | | |
|---|---|---|---|---|---|---|---|---|---|---|---|
| | | | Week 1 Day | | | Week 2 Day | | | Week 3 Day | | |
| | | | 1 | 3 | 7 | 1 | 3 | 7 | 1 | 3 | 7 |
| 25 | 1 | 500 | 4 | 2 | 0 | 4 | 3 | 3 | 3 | NM | NM |
| 26 | 1 | 450 | 4 | 3 | 0 | 4 | 3 | 4 | 4 | NM | NM |
| 27 | 1 | 350 | 4 | 4 | 4 | 4 | 4 | 4 | 4 | NM | NM |
| 28 | 1 | 300 | 4 | 4 | 4 | 4 | 4 | 4 | 4 | NM | NM |
| 29 | 1 | 250 | 4 | 4 | 4 | 4 | 4 | 4 | 4 | NM | NM |
| 30 | 1 | 200 | 4 | 4 | 4 | 4 | 4 | 4 | 4 | NM | NM |
| S | BT | 500 | 1 | 0 | 0 | 2 | 0 | 0 | 2 | 0 | 0 |
| T | BT | 450 | 1 | 0 | 0 | 3 | 1 | 0 | 3 | 3 | 3 |
| U | BT | 350 | 2 | 0 | 0 | 4 | 3 | 4 | 4 | NM | NM |
| V | BT | 300 | 3 | 3 | 0 | 4 | 4 | 4 | 4 | NM | NM |
| W | BT | 250 | 4 | 4 | 4 | 4 | 4 | 4 | 4 | NM | NM |
| X | BT | 200 | 4 | 4 | 4 | 4 | 4 | 4 | 4 | NM | NM |
| Y | NIL | NIL | 4 | 4 | 4 | 4 | 4 | 4 | 4 | 4 | 4 |

Notes to Table Four
a, b and c are all as defined in Notes to Table One.
NM is as defined in Notes to Table Three.

We claim:

1. A package comprising: a particular solid comprising (a) from 10 to 45 weight percent of an isothiazolinone or an isothiazolothione derivative, or a salt or complex thereof, (b) from 10 to 50 weight percent of a water-soluble inorganic salt which does not form a water insoluble salt or water insoluble complex with the said isothiazolinone or isothiazolothione or salt or complex thereof; and (c) from 10 to 45 percent of absorbed water, contained in a bag formed of a water-soluble material.

2. The package of claim 1 wherein the bag is formed from a polyethylene oxide, methyl cellulose, polyvinyl alcohol or polyvinyl acetate.

3. The solid of claim 1 in which component (a) is a compound of general formula:

$$\begin{array}{c} X \\ \| \\ A \diagdown C \diagdown \\ \| \quad N-R \\ C \diagup \\ D \diagup S \end{array}$$

or a salt complex thereof; wherein
X is an oxygen or sulphur atom;
R is a hydrogen atom, a substituted or unsubstituted hydrocarbyl group, a substituted or unsubstituted hydrocarbyloxy group or a carbamoyl group;
A is a hydrogen atom, a halogen atom, a cyano group, or a substituted or unsubstituted hydrocarbyl group;
D is a hydrogen atom, a halogen atom, a cyano group, or a substituted or an unsubstituted hydrocarbyl group; or
A and D, together with the carbon atoms to which they are attached, form a five- or six-membered hydrocarbon ring or a ring which contains a nitrogen heteroatom, which ring may optionally be substituted with halogen, alkyl, alkoxy or alkylthio groups.

4. The solid of claim 3 wherein component (a) is a compound in which X is an oxygen atom.

5. The solid of claim 4 wherein component (a) is 1,2-benzisothiazolin-3-one or a salt or complex thereof.

6. The solid of claim 5 wherein component (a) is an alkali metal salt of 1,2-benzisothiazolin-3-one.

7. The solid of claim 1 wherein component (b) is such as to buffer the pH of an aqueous solution obtained from the solid at a value at which component (a) is soluble and is stable.

8. The solid of claim 7 wherein component (b) is disodium hydrogen phosphate.

9. The solid of claim 1 which also contains a de-dusting agent.

10. The solid of claim 1 which contains the sodium salt of 1,2-benzisothiazolin-3-one, disodium hydrogen phosphate, water and a de-dusting agent.

11. The solid of claim 10 which contains 25 to 40% by weight of the sodium salt of 1,2-benzisothiazolin-3-one; 20 to 35% by weight of disodium hydrogen phosphate; 20 to 40% by weight of water and 0.5 to 1.5% by weight of a de-dusting agent.

12. The solid of claim 1 which has a mean particle size in the range 100 to 500 micrometers.

* * * * *